United States Patent
Prakash et al.

(10) Patent No.: US 8,221,418 B2
(45) Date of Patent: Jul. 17, 2012

(54) ENDOSCOPIC INSTRUMENT FOR TISSUE IDENTIFICATION

(75) Inventors: Mani N. Prakash, Boulder, CO (US); Timothy J. Bahney, Portland, OR (US); Darren Odom, Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 635 days.

(21) Appl. No.: 12/366,298

(22) Filed: Feb. 5, 2009

(65) Prior Publication Data
US 2010/0036379 A1 Feb. 11, 2010

Related U.S. Application Data

(60) Provisional application No. 61/026,788, filed on Feb. 7, 2008.

(51) Int. Cl.
*A61B 18/18* (2006.01)
(52) U.S. Cl. .......................................................... 606/51
(58) Field of Classification Search ............... 604/22; 600/372; 607/122; 606/41, 48, 50, 32
See application file for complete search history.

(56) References Cited

U.S. PATENT DOCUMENTS

| | | | |
|---|---|---|---|
| 4,543,959 A | 10/1985 | Sepponen | |
| 5,460,182 A | 10/1995 | Goodman et al. | |
| 5,500,012 A * | 3/1996 | Brucker et al. | 607/122 |
| 5,762,609 A | 6/1998 | Benaron et al. | |
| 5,762,613 A | 6/1998 | Sutton et al. | |
| 5,769,791 A | 6/1998 | Benaron et al. | |
| 5,772,597 A | 6/1998 | Goldberger et al. | |
| 5,800,350 A * | 9/1998 | Coppleson et al. | 600/372 |
| 5,807,261 A | 9/1998 | Benaron et al. | |
| 5,817,093 A * | 10/1998 | Williamson et al. | 606/50 |
| 5,843,000 A | 12/1998 | Nishioka et al. | |
| 5,961,458 A | 10/1999 | Carroll | |
| 6,484,050 B1 | 11/2002 | Carroll et al. | |
| 6,697,666 B1 | 2/2004 | Richards-Kortum et al. | |
| 6,718,196 B1 | 4/2004 | Mah et al. | |
| 6,881,213 B2 * | 4/2005 | Ryan et al. | 606/41 |
| 7,449,008 B2 | 11/2008 | Hochman | |
| 2003/0004407 A1 | 1/2003 | Carroll et al. | |
| 2003/0045798 A1 | 3/2003 | Hular et al. | |
| 2005/0261568 A1 | 11/2005 | Hular et al. | |
| 2008/0306391 A1 | 12/2008 | Hular et al. | |

OTHER PUBLICATIONS

P.R. Stauffer et al.; "*Phantom and Animal Tissues for Modelling the Electrical Properties of Human Liver*"; International Journal of Hyperthermia, 2003, vol. 19, No. 1, pp. 89-101; Taylor and Francis Healthsciences; United Kingdom.

* cited by examiner

*Primary Examiner* — Manuel Mendez (57) ABSTRACT

The present disclosure relates to various apparatus, systems and methods of identifying and treating tissue using at least one electrical property of tissue. Provided is a method for identifying and treating tissue, the method including providing a electrosurgical treatment device including an electrode assembly for measuring one or more electrical properties of a target tissue, the electrode assembly being mounted on a distal end thereof, measuring the one or more electrical characteristics of the target tissue, comparing the measured electrical property values of the target tissue against electrical property values of known tissue types, identifying a tissue type of the target tissue, adjusting an energy delivery configuration of the electrosurgical treatment device to the type of target tissue, and activating the electrosurgical treatment device to treat the target tissue.

6 Claims, 9 Drawing Sheets

ENDOSCOPIC INSTRUMENT FOR TISSUE IDENTIFICATION

CROSS-REFERENCE TO RELATED APPLICATIONS

This application claims the benefit of priority to U.S. Provisional Application Ser. No. 61/026,788 entitled "ENDOSCOPIC INSTRUMENT FOR TISSUE IDENTIFICATION" filed Feb. 7, 2008 by Mani N. Prakash et al, which is incorporated by reference herein.

BACKGROUND

1. Technical Field

The present disclosure relates to open or endoscopic instruments and method for treating tissue, and more particularly, the present disclosure relates to surgical instruments including an assembly for determining tissue type and the condition of the tissue being treated utilizing electrical property measurements of the tissue.

2. Background of Related Art

A hemostat or forceps is a simple plier-like tool that uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Over the last several decades, more and more surgeons are complementing traditional open methods of gaining access to vital organs and body cavities with endoscopes and endoscopic instruments that access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

As mentioned above, by utilizing an electrosurgical instrument, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

Bipolar electrosurgical instruments are known in the art, as are other electrosurgical instruments. Commonly owned U.S. Patent Application Publication No. 2007-0062017, discloses a bipolar electrosurgical instrument. Conventional bipolar electrosurgical instruments may include a cutting blade, fluid applicator, stapling mechanism or other like feature, in various combinations.

Different types of tissues, i.e. vessels, ligaments, may require different energy delivery configurations to effect proper sealing. While a specific energy delivery configuration may be adequate for treating an artery or vein, the same energy delivery configuration may not be suitable for treating a ligament. Although a majority of the time the type of tissue being treated is either known or visually apparent, there may be instances where a surgeon is unable to visually determine the type of tissue being sealed. Treating non-target type tissue with an energy configuration configured for a target type tissue may cause damage to the non-target tissue and/or result in failure to effect proper treatment.

Traditional methods for identifying tissue within the body are based on sensing physical characteristics or physiological attributes of body tissue, and then distinguishing normal from abnormal states from changes in the characteristic or attribute. For example X-ray techniques measure tissue physical density, ultrasound measures acoustic density, and thermal sensing techniques measures differences in tissue heat. A measurable electrical property of tissue is its impedance; i.e., the resistance tissue offers to the flow of electrical current through it. Values of electrical impedance of various body tissue are well known through studies on intact human tissue or from excised tissue made available following therapeutic surgical procedures.

Various methods and apparatus for measuring tissue electrical properties are known. For example, U.S. Pat. No. 5,380,429 to Withers, discloses a method and apparatus for displaying multi-frequency bio-impedance, and U.S. Patent Publication No. 2006/0004300, discloses a method of multi-frequency bio-impedance determination.

Once the type of tissue is identified, determining the condition or state of the tissue is important in effectively and properly treating the tissue. Diseased, ischemic, or otherwise compromised tissue may not adequately seal, or may require alteration to the energy delivered to the tissue. It is well documented that a decrease in electrical impedance occurs in tissue as it undergoes cancerous changes. Using any of the known methods for measuring tissue impedance, the tissue impedance may be measured, and the resulting measurements may be compared against known impedance measurements for like tissue. Difference between the readings may be used to indicate the condition of the tissue. Thus, knowledge of the electrical properties of tissue may be used to identify the type of tissue and/or the condition of that tissue.

SUMMARY

The present disclosure relates to surgical instruments including an assembly for determining tissue type and the condition of the tissue being treated utilizing tissue electrical property measurements.

Provided is a bipolar forceps including a handle, a shaft extending from the handle and having opposing jaw members at a distal end thereof, wherein the jaw members are configured for sealing tissue, and an electrode assembly for measuring an electrical property of a target tissue, the electrode assembly being mounted on at least one of said opposing jaw members.

The electrode assembly includes a plurality of electrodes and is configured to be operably connected to a processing unit. The processing unit may be configured to selectively measure at least one of an impedance, conductance and capacitance of the target tissue. The processing unit may be configured to determine a type of target tissue and/or a condition of the target tissue. The processing unit may be configured to alert a user when a predetermined condition has been satisfied. The forceps may be operably connectable to a generator. The generator may include a processing unit for determining tissue impedance.

Also provided is a method for identifying and treating tissue including providing a electrosurgical treatment device including an electrode assembly for measuring one or more electrical properties of a target tissue, the electrode assembly being mounted on a distal end thereof, measuring the one or more electrical characteristics of the target tissue, comparing the measured electrical property values of the target tissue against electrical property values of known tissue types, identifying a tissue type of the target tissue, adjusting an energy delivery configuration of the electrosurgical treatment device to the type of target tissue, and activating the electrosurgical treatment device to treat the target tissue.

The electrode assembly may include one or more electrodes. The electrode assembly includes a base having an electrode extending coaxially therethrough. The coaxially extending electrode may be operably connected to a high frequency generator. The high frequency generator may be capable of generating a frequency between 30 MHz and 30 GHz. The method may further include measuring an electrical property of the target tissue following treatment, and the determining the effectiveness of the treatment.

Further provided is a system for identifying and treating tissue including an electrosurgical treatment device, a generator operably connected to the electrosurgical treatment device for delivering electrosurgical energy thereto, an electrode assembly extending from a distal end of the electrosurgical treatment device, and a processing unit operably connected to the electrode assembly for measuring tissue one or more electrical properties of the tissue. The electrode assembly may be selectively extendable from the distal end of the electrosurgical treatment device and may include an electrode extending coaxially therethrough. The electrode may be operably connected to a high frequency generator. The electrode assembly may instead include at least a pair of electrodes or an array of electrodes.

A system for identifying tissue is also provided including a housing, an elongated body extending distally therefrom, the elongated body defining at least one lumen therethrough, and a probe operably extendable through the at least one lumen, the probe including at least one electrode determining at least one electrical property of tissue. The at least one electrode may extend coaxially through the probe. The system may further include a processor configured for identifying tissue using the determined electrical property. The array of electrodes may include at least four electrodes arranged linearly. The array of electrodes may instead include a plurality of electrodes arranged in an array.

BRIEF DESCRIPTION OF THE DRAWINGS

Various embodiments of the subject instrument are described herein with reference to the drawings wherein.

DETAILED DESCRIPTION

Referring now to FIGS. 1-4, an embodiment of an electrosurgical instrument according to the present disclosure is shown generally as bipolar forceps 100. Bipolar forceps 100 include a housing 120, a handle assembly 130, a rotating assembly 180, a trigger assembly 170 and an end effector assembly 110 that mutually cooperate to grasp, seal and divide tubular vessels and vascular tissue. Although the following disclosure focuses predominately on discussion of a bipolar forceps 100 for use in connection with endoscopic surgical procedures, an open forceps 100' are also contemplated for use in connection with traditional open surgical procedures and are shown by way of example in FIG. 1B. For the purposes herein, the endoscopic version is discussed in detail; however, it is contemplated that open forceps 100' also include the same or similar operating components and features as described below.

Figure 1A:
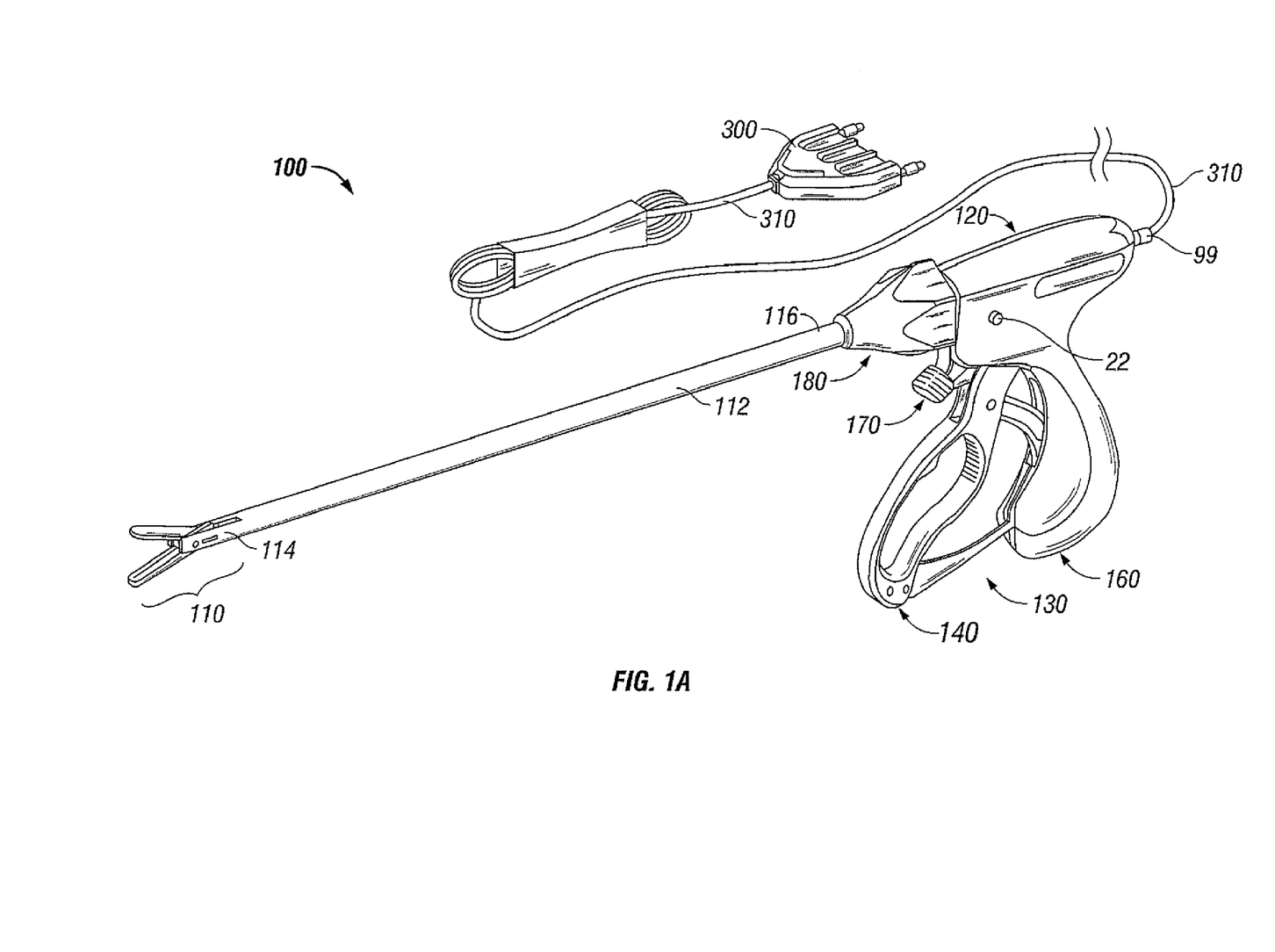
FIG. 1A is a left, perspective view of an endoscopic bipolar forceps including a multi-electrode assembly for measuring tissue impedance according to an embodiment of the present disclosure.
Figure 1B:
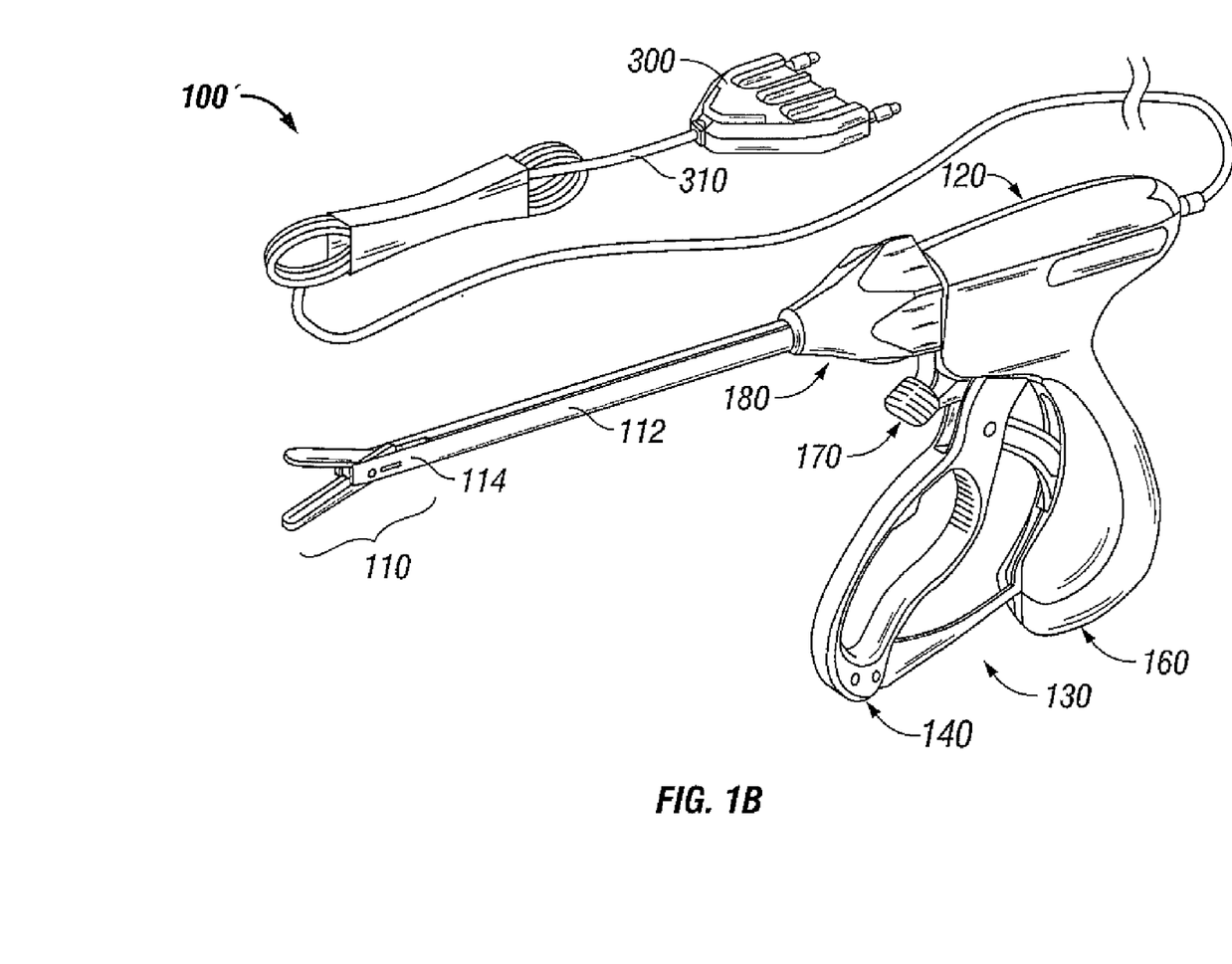
FIG. 1B is a left, perspective of an open bipolar forceps including a multi-electrode assembly for measuring tissue impedance according to an embodiment of the present disclosure.

Bipolar forceps 100, 100' are substantially identical in form and function to bipolar forceps 10, 10' described in detail in commonly owned, U.S. Patent Publication No. 2007-0062017. Thus, the form and function of bipolar forceps 100, 100' will be discussed only to the extent necessary to describe the improvement thereto. The aspects of the present disclosure may be incorporated into any suitable electrosurgical instrument.

Figure 2:
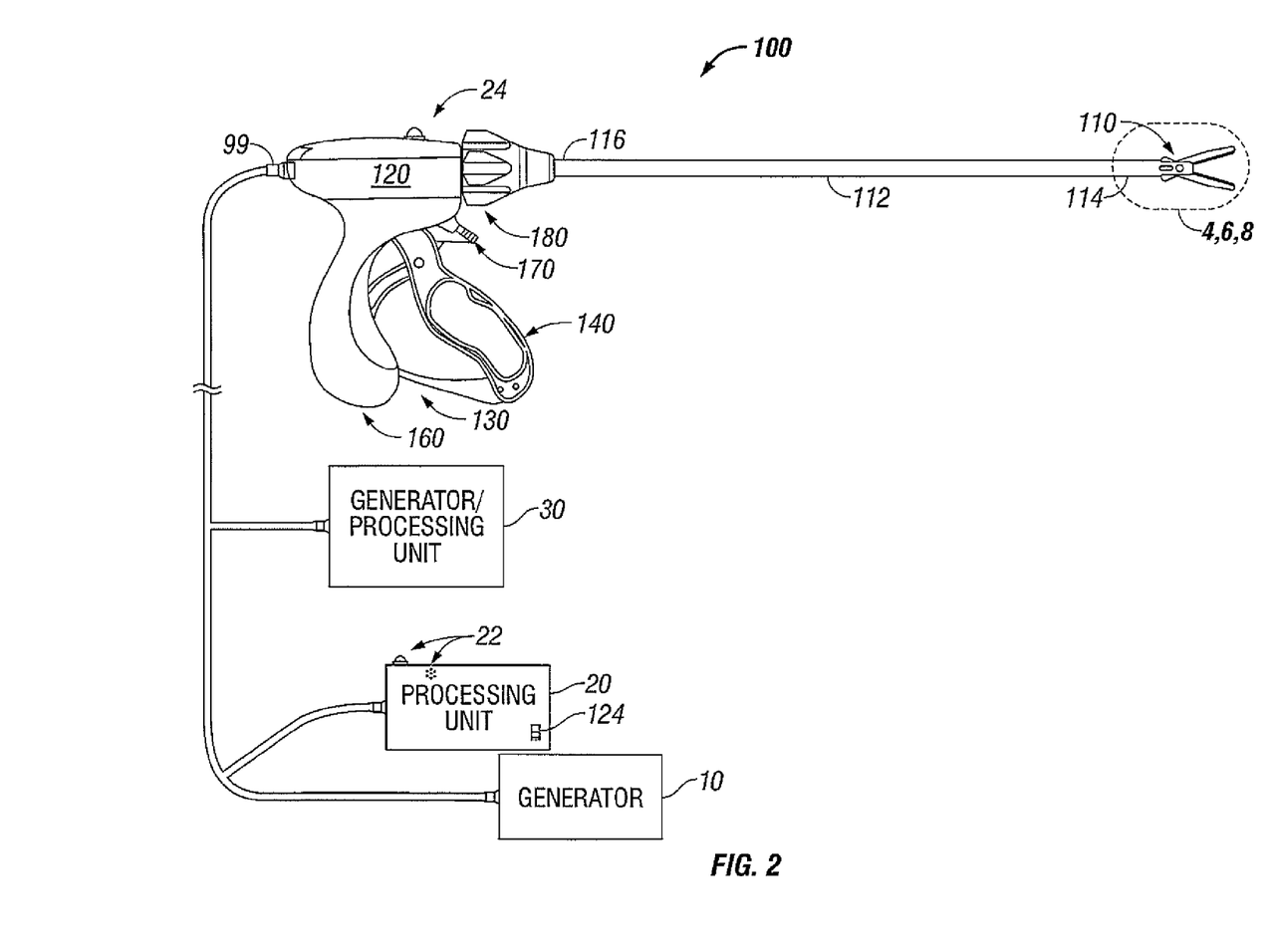
FIG. 2 is a schematic illustration of an electrosurgical system including the endoscopic bipolar forceps of FIG. 2A.

Turning now to FIGS. 1A and 2, forceps 100 includes a shaft 112 that has a distal end 114 dimensioned to mechanically engage the end effector assembly 110 and a proximal end 116 that mechanically engages housing 120. In the drawings and in the descriptions that follow, the term "proximal", as is traditional, will refer to the end of the forceps 100 that is closer to the user, while the term "distal" will refer to the end which is further from the user.

As seen in FIG. 1A, handle assembly 130 includes a fixed handle 160 and a movable handle 140. Fixed handle 160 is integrally associated with housing 120 and handle 140 is movable relative to fixed handle 160. Rotating assembly 80 is preferably attached to a distal end of housing 120 and is rotatable approximately 180 degrees in either direction about a longitudinal axis "A".

Figure 3:
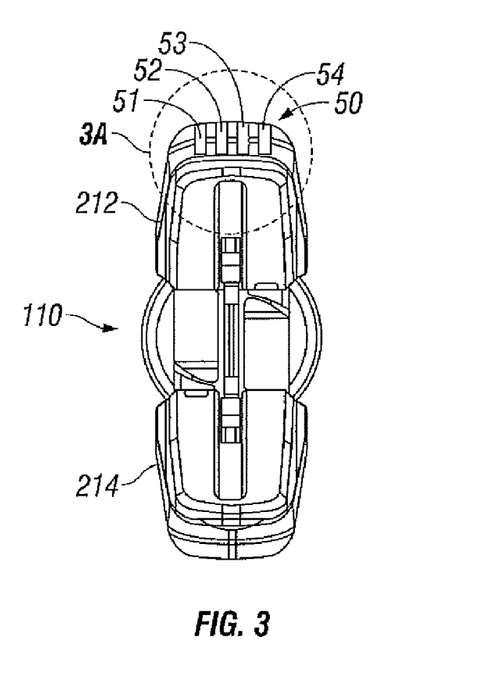
FIG. 3 is an enlarged front view of a jaw member including the multi-electrode assembly.
Figure 3A:
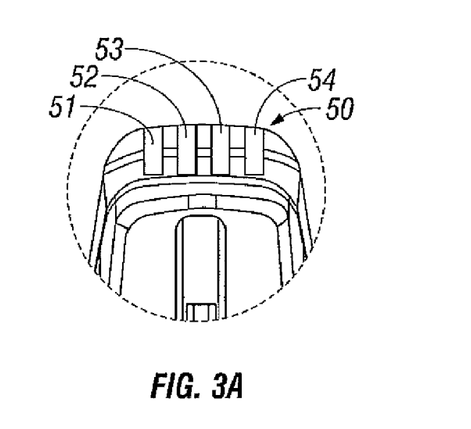
FIG. 3A is an enlarged view of the indicated area of detail of FIG. 3.
Figure 4:
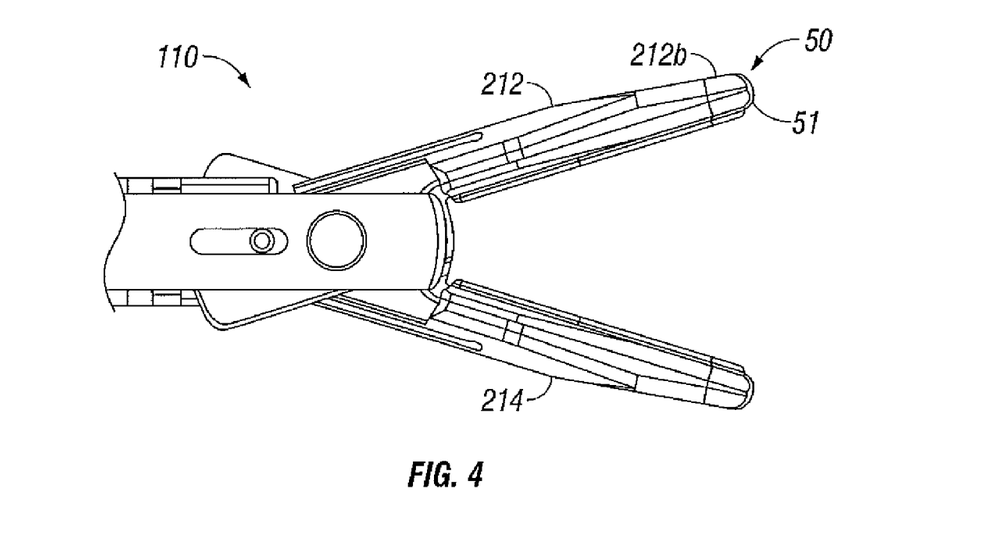
FIG. 4 is a side elevational view of the jaw member of FIG. 3.

Turning briefly to FIGS. 3-4, end effector assembly 110 includes first and second jaw members 212, 214. First and second jaw members 212, 214 are operably connected to handle 140 (FIG. 1A). First and second jaw members 212, 214 are configured to approximate towards one another upon activation of handle 140. First and second jaw members 212, 214 cooperate to grasp and seal target tissue therebetween.

As best seen in FIGS. 1A and 2, forceps 100 also include an electrical interface or plug 300 that connects the forceps 100 to a source of electrosurgical energy, e.g., a generator 10, and a processing unit 20. Generator 10 and processing unit 20 may be combined to form a single generator/processing unit 30. For ease of disclosure, further references to processing unit 20 may also be applicable to generator/processing unit 30. Generator 10 may be one of many sold by Valleylab—a division of Tyco Healthcare LP, located in Boulder Colo., used as a source of electrosurgical energy, e.g., FORCE EZ™ Electrosurgical Generator, FORCE FX™ Electrosurgical Generator, FORCE 1C™, FORCE 2™ Generator, SurgiStat™ II. One such system is described in commonly-owned U.S. Pat. No. 6,033,399 entitled "ELECTROSURGICAL GENERATOR WITH ADAPTIVE POWER CONTROL". Other systems have been described in commonly-owned U.S. Pat. No. 6,187,003 entitled "BIPOLAR ELECTROSURGICAL INSTRUMENT FOR SEALING VESSELS".

Generator 10 and/or generator/processing unit 30 may include various safety and performance features including isolated output, independent activation of accessories, and the Valleylab REM™ Contact Quality Monitoring System, which may substantially reduce the risk of burns under the patient return electrode. The electrosurgical generator may include Valleylab's Instant Response™ technology features that provides an advanced feedback system that senses changes in tissue 200 times per second and adjusts voltage and current to maintain appropriate power.

Processing unit 20 is operably connected to an electrode assembly 50 (FIG. 3). As will be discussed in further detail below, electrode assembly 50 may be mounted on a distal end of forceps 100. Processing unit 20 operates in a manner similar to known tissue impedance measuring devices. Briefly, a predetermined energy signal is produced by processing unit 20 and applied to the target tissue (not explicitly shown) through electrode assembly 50. The resultant electrical response of the tissue to the signal may then be measured and converted into an impedance value. By comparing the tissue impedance measurements with known tissue impedance measurements processing unit 20 may determine the type of tissue being in contact with electrode assembly 50.

The electrical current produced by processing unit 20 may vary depending on the type of tissue being identified. Processing unit 20 may configured to produce AC and/or DC current. Processing unit 20 may be configured to generate an electrical signal having a frequency ranging from RF (100 kHz) upwards of microwaves (low MHz to GHz). Depending on the application processing unit 20 may produce a signal of constant frequency, or may instead perform a frequency sweep. Bipolar forceps 100 may include more than one electrode assembly 50 connected to processing unit 20 for measuring tissue impedance. As will be discussed in further detail below, the one or more electrode assemblies 50 may include different electrode configurations depending on the tissue type and/or signal frequency being tested. Processing unit 20 may include any suitable methods of increasing the accuracy and consistency of the tissue electrical property measurements, e.g. filters and multi-frequency readings.

Processing unit 20 may operate in a number of modes. Processing unit 20 may be configured to alert a user when electrode assembly 50 has contacted a specific tissue type. In this manner, a user would set processing unit 20 to scan for a particular tissue type. Processing unit 20 would produce an electrical signal configured for best identifying the tissue type. The electrical signal produced by processing unit 20 may be manually determined by the user or may instead be automatically determined by processing unit 20. The electrical signal produced may include a specific frequency or range of frequencies and/or may include a specific signal configuration. Electrode assembly 50 may be placed in contact over a portion of tissue. As electrode assembly 50 contacts tissue of the target type, as determined by processing unit 20 by comparing the electrical property measurements with known electrical property measurements of like tissue, processing unit 20 may alert the user. The alert may be audio and/or visual. An audio and/or visual indicator 22, 24 (FIG. 2) may be included in/on processing unit 20 and/or bipolar forceps 100.

Identifying tissue type by comparing the electrical property measurements of the tissue with electrical property measurements from known tissue type requires the availability of electrical property measurements of known tissue. These measurements may not always be available, or may vary depending on the environment in which the target tissue is situated. For example, tissue located within the digestive tract and exposed to digestive enzymes may have different electrical property measurements from tissue exposed to air. When implementing the comparative technique described above, knowledge of the electrical property of the tissue exposed to digestive enzymes would be of little use when compared to the electrical properties of tissue exposed to air. When electrical property measurements of known tissue are not available, the type of tissue may be determined by comparing the electrical property measurements of the target tissue with the electrical property measurements of the surrounding tissue. Since fat exhibits different electrical properties from muscle, and muscles exhibits different electrical properties that connective tissue, by comparing the relative electrical property measurements of different tissue types within the same environment, i.e. saturated in digestive enzymes, or exposed to air, the differences in the relative electrical property measurements of the various tissues may be used to distinguish the various tissue types. Another example is the difference between a suspicious mass and the surrounding normal tissue may be used to determine its nature as benign or malignant.

Alternatively, processing unit 20 may be configured to determine the type of tissue in contact with electrode assembly 50. In this manner, processing unit 20 produces an electrical signal spanning a wide range of frequencies and/or wave configurations. The range of frequencies and/or wave configurations may be limited by the user. As before, the tissue electrical property measurements (magnitude and/or phase) are compared against electrical property measurements for known tissue. Once processing unit 20 has determined the type of tissue the user may be alerted. The alert may be audio and/or visual.

Once the type of tissue is known, whether through visual inspection or tissue impedance measurements, the condition of the tissue may also be determined. Using techniques similar to that described above, the condition of the tissue may also be determined. Knowing the type of tissue being examined is not necessary; however, it permits a user to limit the frequency range and/or signal configuration of the electrical signal applied to the tissue, thereby reducing the time for a result. The condition of the tissue may be determined by comparing the electrical property measurements with electrical property measurements of tissue of a known condition. In addition, the condition of the tissue may be determined by comparing the electrical property measurements of portions of the same tissue. Processing unit 20 may provide the user with an audio and/or visual alert as to the condition of tissue in contact with electrode assembly 50.

Tissue has many electrical properties and there are many known methods for measuring these electrical properties. Although the following discussion will relate to a four-electrode method of measuring tissue impedance, other methods of measuring tissue electrical properties have been contemplated by the present disclosure. In the four-electrode method, four equidistant electrodes are placed in contact with or penetrate into the tissue to be tested. In one procedure utilizing the four-electrode method, a sinusoidal voltage is applied to the tissue across two electrodes and the resultant sinusoidal current flow through the tissue is measured. The magnitude of the tissue impedance may be determined as the ratio of the root-mean-square (RMS) voltage and the current values. The phase angle of the tissue impedance may be determined as the delay in radians of the peak sinusoidal current with respect to the peak sinusoidal voltage. By comparing the resulting impedance values with known values for various body tissue, the tissue type may be determined. It should be appreciated that the aspects of the present disclosure should not be limited to the methods of determining tissue impedance disclosed herein. Any suitable method for measuring tissue electrical properties may be incorporated into the embodiments of the present disclosure.

Turning now to FIGS. 3-8, various embodiments of opposing jaw members including one or more multi-electrode assemblies that operate in a manner as discussed above are shown. Referring initially to FIGS. 3- 4, end effector 110 of bipolar forceps 100 includes an electrode assembly 50. Electrode assembly 50 is mounted on a distal end 212b of first jaw member 212. As will be discussed below, alternate embodiments of bipolar forceps 100 may include a plurality of electrode assemblies mounted at various locations on first and/or second jaw members 212, 214. Electrode assembly 50 includes four electrodes 51, 52, 53, 54. In the illustrated embodiment, electrodes 51, 52, 53, 54 form substantially planar members having a substantially similar size and configuration. Electrodes 51, 52, 53, 54 are spaced an equidistance apart and may be formed of a metal, an alloy or other suitable material. Electrodes 51, 52, 53, 54 of electrode assembly 50 are operably connected to processing unit 20 (FIG. 3).

In operation, electrodes 51, 52, 53, 54 of electrode assembly 50 are placed in contact with the tissue to be identified. First and second jaw members 212, 214 may be in an open or closed condition. Processing unit 20 produces an electric signal that is directed into the target tissue through outer electrodes 51, 54. Processing unit 20 may be configured to continuously produce a signal, or instead bipolar forceps 100 may include a button or lever 122, 124 mounted on housing 120 (FIG. 1A) and/or processing unit 20 (FIG. 2) for activating processing unit 20. As discussed above, depending on the application, the electric signal may be of a specific frequency or range of frequencies and of any configuration. The respective portion of tissue disposed between outer electrode 51 and inner electrode 52, and outer electrode 54 and inner electrode 53 functions to complete a circuit path therebetween. These portions of tissue produce characteristic tissue responses based on the signals delivered to electrodes 51, 52, 53, 54 by processing unit 20. The resulting tissue response is acquired by inner electrodes 52, 53. Also, as discussed above, the measurements of the tissue response may be used to calculate the tissue impedance. By comparing the tissue impedance values of the target tissue with impedance values of known tissue, the type of tissue being contacted (e.g., lung, liver, muscle, etc.) may be determined.

As discussed above, once the tissue type has been determined, either through visual inspection, by comparing tissue electrical property measurements or with another suitable method, the condition of the tissue may also be determined. By directing an electric signal of a frequency or range of frequencies configured for the particular tissue type being tested and measuring the resultant impedance values, the condition of the tissue may be determined. For example, healthy tissue may be distinguished from cancerous tissue. Additionally, the stage of development of the cancer may also be determinable using the tissue impedance measurements.

Once the tissue type and condition of the tissue have been identified, bipolar forceps 100 may operate as a conventional bipolar vessel sealer. The energy delivery configuration of generator 10 may be adjusted in accordance with the identified tissue type being sealed. The closure pressure of first and second jaw members 212, 214 may also be adjusted in view of the type of tissue being sealed and/or the condition of the tissue being sealed.

While four electrodes, 51, 52, 53, 54 are shown as forming a part of multi-electrode assembly 50, any suitable number of electrodes may be used either greater than or less than four in forming multi-electrode assembly 50.

Figure 5:
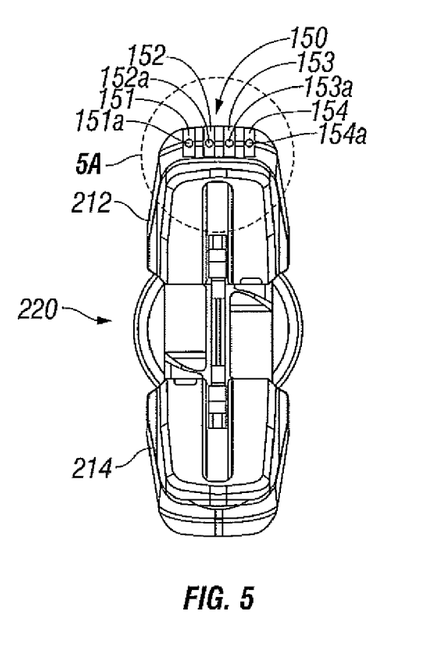
FIG. 5 is an enlarged front elevational view of an alternate embodiment of a jaw member including another multi-electrode assembly for measuring tissue impedance.
Figure 5A:
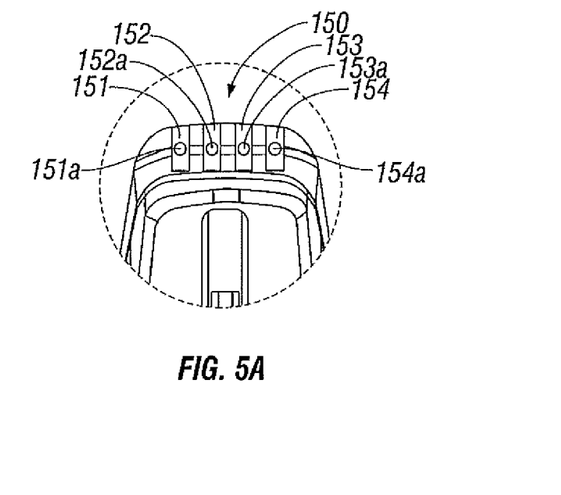
FIG. 5A is an enlarged view of the indicated area of detail of FIG. 5.
Figure 6:
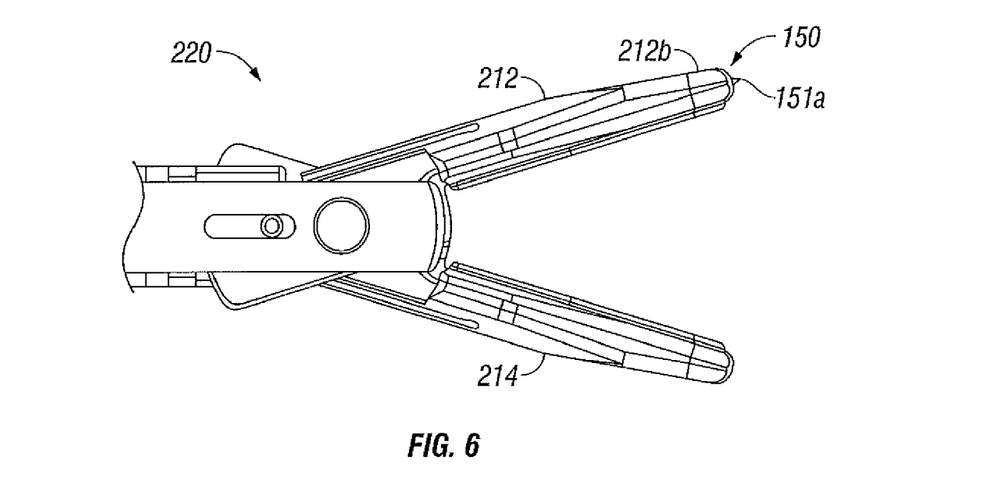
FIG. 6 is a side elevational view of the jaw member of FIG. 5.

Turning now to FIGS. 5-6, in an alternate embodiment of an end effector of the present disclosure, end effector 220 includes electrode assembly 150 mounted on a distal end 212b of first jaw member 212. Alternately, electrode assembly 150 may be mounted on distal end 214b of second jaw member 214. Electrode assembly 150 includes electrodes 151, 152, 153, 154. Electrodes 151, 152, 153, 154 include piercing or penetrating members 151a, 152a, 153a, 154a, respectively, for penetrating the target tissue to be identified. By using piercing members 151, 152, 153, 154 to penetrate the tissue a relatively truer or more accurate tissue impedance measurement may be obtained. Piercing members 151a, 152a, 153a, and 154a may be of any suitable dimension and of any suitable configuration. In an alternate embodiment, electrodes 151, 152, 153, 154 and/or piercing members 151a, 152a, 153a, 154a may be selectively retractable and/or extendable.

Figure 7:
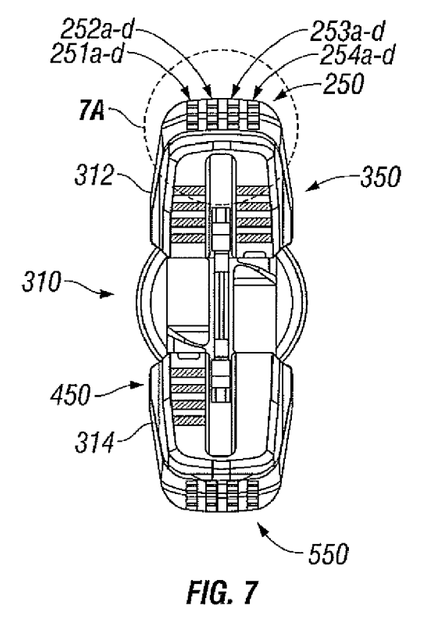
FIG. 7 is an enlarged front elevational view of yet another jaw member according to the present disclosure including yet another multi-electrode electrode assembly.
Figure 7A:
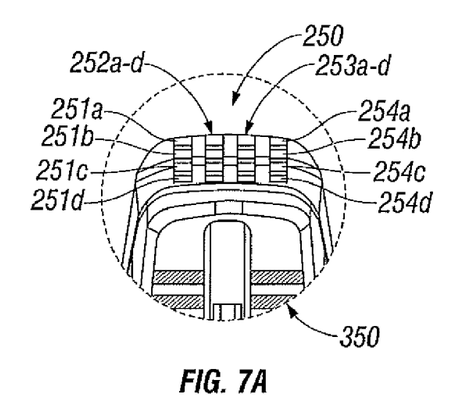
FIG. 7A is an enlarged view of the indicated area of detail of FIG. 7.
Figure 8:
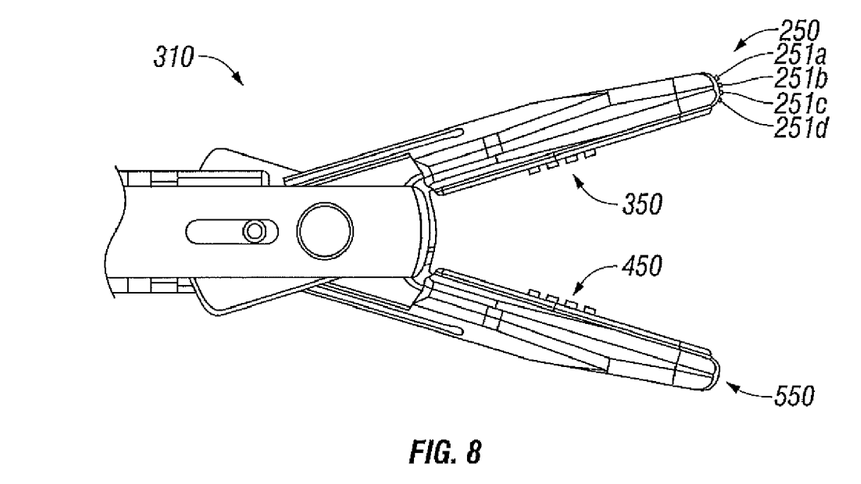
FIG. 8 is a side elevational view of the jaw member of FIG. 7.

With reference now to FIGS. 7-8, in another embodiment of an end effector of the present disclosure, end effector 310 includes electrode assembles 250, 350, 450, and 550. Electrode assemblies 250, 550 are each substantially similar to electrode assemblies 50, 150 described hereinabove, and will therefore only be described as relates to the differences therebetween. Electrode assembly 250 or 550 includes an array of electrodes 251a-d, 252a-d, 253a-d, 254a-d arranged in any suitable configuration (e.g. rectilinear) and in any suitable quantity. Electrodes 251a-d, 252a-d, 253a-d, 254a-d of electrode assembly 250 are each operably connected to processing unit 20 (FIG. 2). Processing unit 20 may be configured to selectively apply electric signals through any or all of electrodes 251a-d, 252a-d, 253a-d, 254a-d in a manner similar to that described above to determine impedance of a target tissue. The rectilinear array of electrode assembly 240 enables a user to select the electrode configuration best suited for measuring and identifying tissue of a particular type.

With continued reference to FIGS. 7-8, electrode assemblies 350, 450 are positioned on an inner surface of first and second jaw member 312, 314, respectively, e.g., on a tissue contacting surface thereof. Electrode assemblies 350, 450 operate in a manner substantially similar to electrode assemblies 250, 550 described hereinabove. By including electrode assemblies 350, 450 on an inner surface of first and second jaw member 312, 314, respectively, the type of tissue being grasped therebetween may be determined. Such identification of tissue may occur at any time prior to a sealing of the target tissue.

Electrode assemblies 50, 150, 250, 350, 450, 550 may also be used post-sealing to determine if a proper seal has been formed. By measuring the impedance of a post-sealing tissue, and comparing the impedance measurements thereof with known values of properly sealed tissue processing unit 20 (FIG. 2) may alert a user of the condition of the post-sealing tissue. Alternatively, processing unit 20 may compare the post-sealing impedance measurements of the tissue with the pre-sealing impedance measurements thereof to determine if a proper seal has been affected.

Referring now to FIGS. 9-12, another embodiment of the present disclosure is shown generally as endoscopic device 500. Briefly, endoscopic device 500 includes a housing 520 and an elongated tubular member 512 extending from the housing 520. Tubular member 512 defines a plurality of working channels or lumens 515a, 515b, 515c extending therethrough. Proximal end 516 of tubular member 512 mechanically engages or is supported on or by housing 520. Tubular member 512 may be rigid, flexible and/or selectively rigid. Housing 520 may include a steering mechanism 580 for controlling or articulating distal end 514 of tubular member 512 in any suitable manner. Working channels or lumens 515a, 515b, 515c may be configured to receive an endoscope, electrosurgical instrument, snare or the like therethrough.

Figure 9:
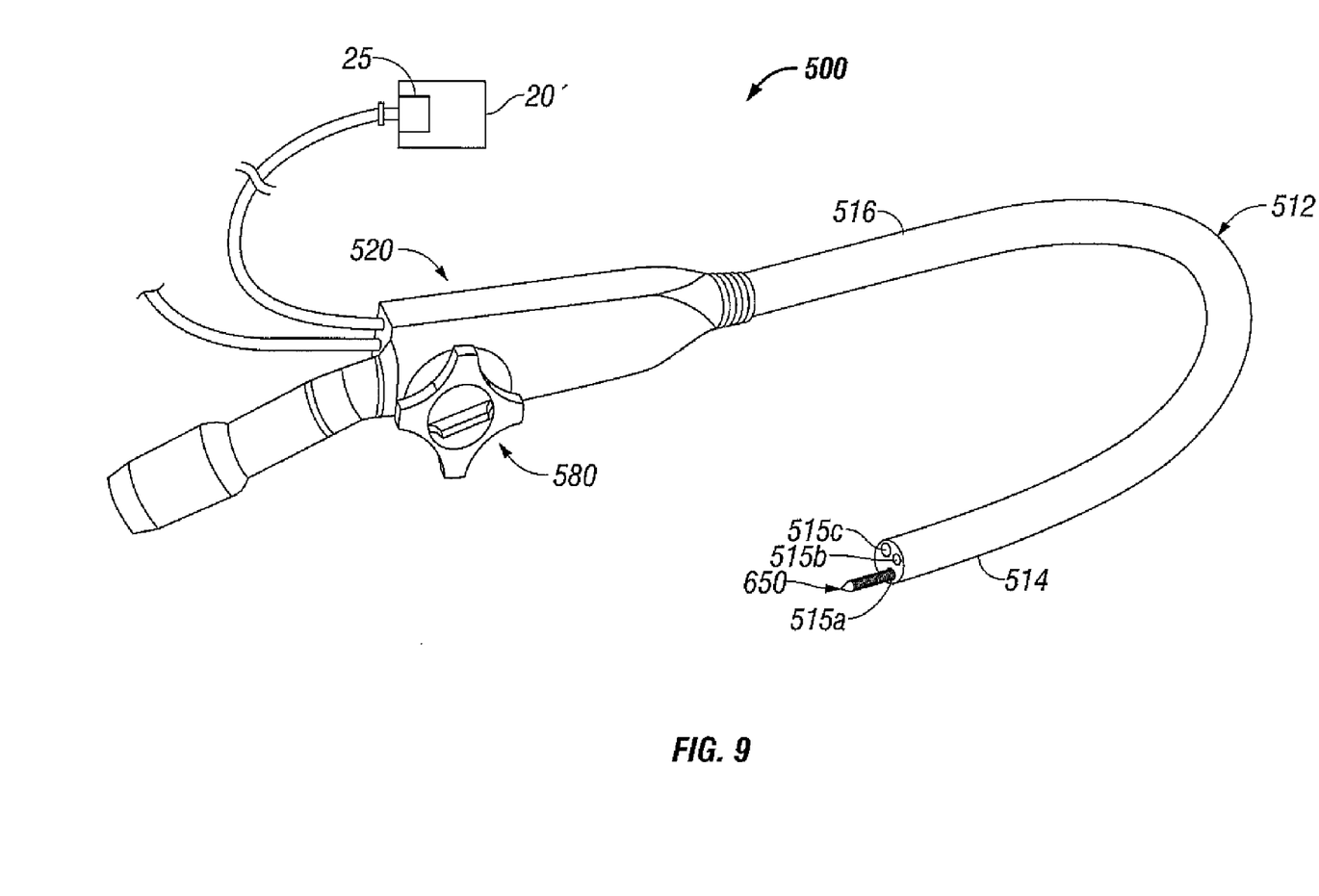
FIG. 9 is a perspective view of an alternate embodiment of an electrosurgical instrument extending through a working channel of an endoscope.
Figure 10:
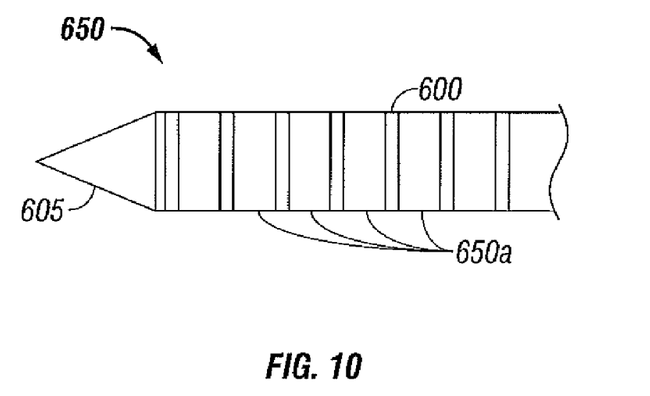
FIG. 10 is a enlarged side view of the electrode assembly of the endoscopic device of FIG. 9.

As seen in FIG. 9, an electrode assembly 650 extends through working channel or lumen 515a of tubular member 512. As seen in FIG. 10, electrode assembly 650 includes a plurality of electrodes 650a mounted about a probe-like base or core member 600. Electrodes 650a may be axially spaced apart from one another along a length of core member 600. Electrode assembly 650 may include a cauterization and/or sealing tip 605 for treating tissue. As seen in FIG. 10, tip 605 may be sharpened, tapered and/or beveled.

Electrode assembly 650 is operably connected to a processing unit 20' (see FIG. 9). Processing unit 20' is substantially similar to processing unit 20 described hereinabove and thus will not be described in further detail herein. Additionally, processing unit 20' may include a drive mechanism 25 for advancing and retracting multi-electrode assembly 650 from within channel 515a of tubular member 512.

Figure 11:
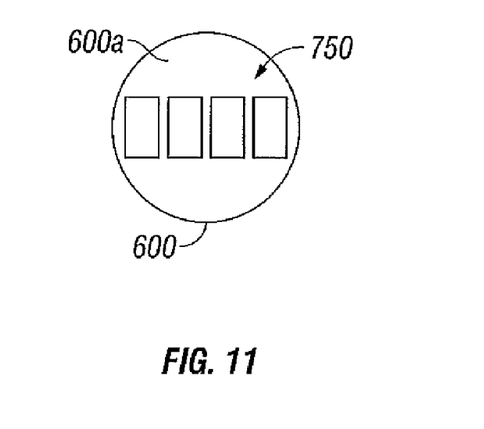
FIG. 11 is an enlarged end view of an alternate embodiment of an electrode assembly.
Figure 12:
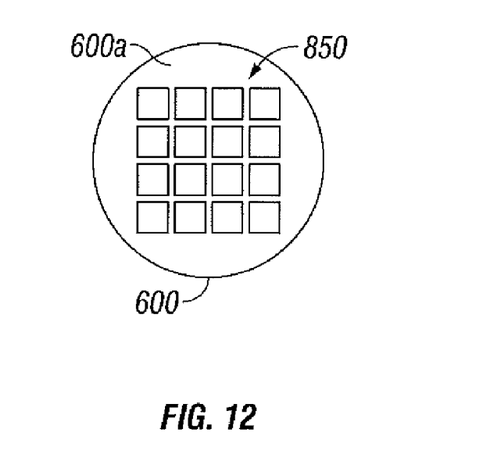
FIG. 12 is an enlarged end view of another embodiment of an electrode assembly.

Alternatively, as seen in FIGS. 11 and 12, base or core member 600 may include a flattened distal end surface 600a. Flattened distal end surface 600a may include multi-electrode assemblies of multiple configurations. As shown in FIG. 11, base member 600 may include a linear array of electrodes 750 provided on distal end surface 600a (e.g., an exemplary four electrodes being shown), or a grid-like or rectangular array of electrodes 850 provided on distal end surface 600a (e.g., an exemplary 4×4 rectangular array being shown) multi-electrode assembly 850. Electrode arrays 750, 850 operate in a manner similar to the multi-electrode assemblies or arrays described above and thus will not be described in further detail herein.

Figure 13A:
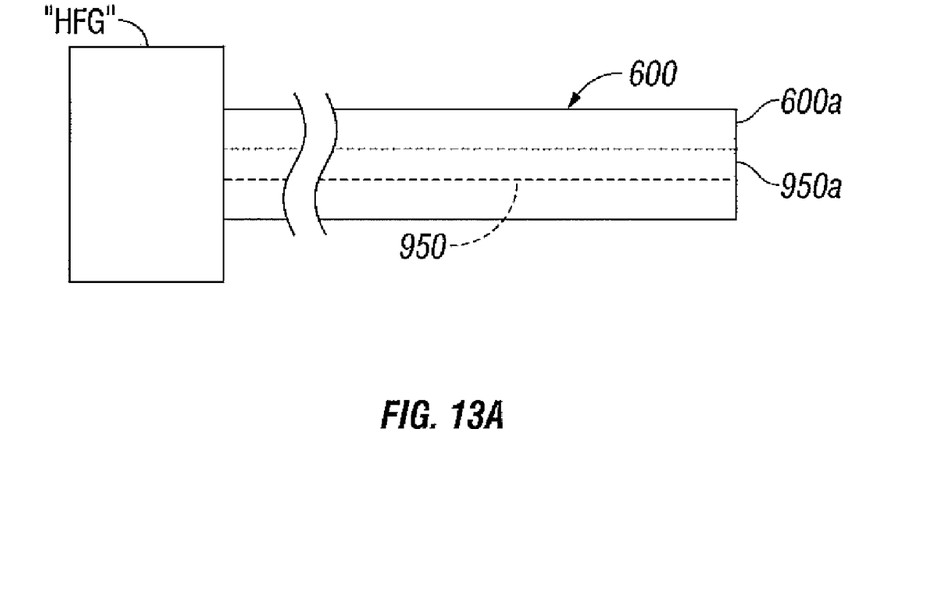
FIG. 13A is a side view of another embodiment of an electrode assembly.
Figure 13B:
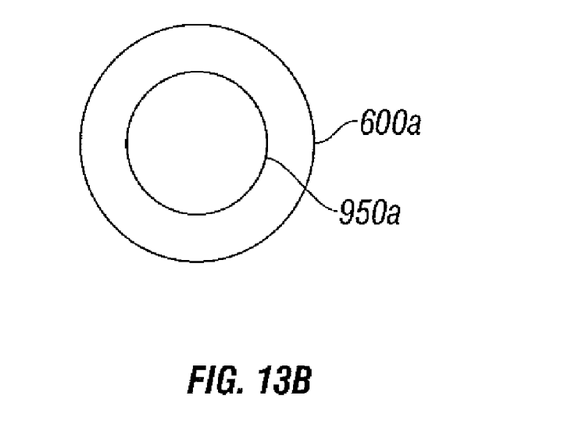
FIG. 13B is an enlarged distal end view of the electrode assembly of FIG. 13A.

With reference to FIGS. 13A and 13B, in yet another embodiment, base member 600 defines a sheath 602 that includes a coaxially electrode 950 extending a length thereof. In this manner, only a distal end 950a of electrode 950 is exposed. It is envisioned that distal end 950a of electrode 950 may form a pointed surface for penetrating tissue. Coaxially electrode 950 may be operably connected to a high frequency generator "HFG" capable of generating a signal between 30 MHz-30 GHz.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto. For example,

What is claimed is:

1. A method for identifying and treating tissue, the method comprising the steps of:
providing an electrosurgical treatment device including an electrode assembly configured to measure one or more electrical properties of a target tissue;
applying an electrical signal having at least one of a range of frequencies and a range of wave configurations to the target tissue;
measuring the one or more electrical properties of the target tissue in response to the electrical signal;
comparing values of the measured electrical properties of the target tissue against values of electrical properties of known tissue types;
identifying a type of the target tissue based on the comparison;
adjusting at least one of the range of frequencies and the range of wave configurations of the electrical signal based on the identified tissue type;
applying the adjusted electrical signal to the target tissue;
measuring the one or more electrical properties of the target tissue in response to the adjusted electrical signal;
comparing values of the measured electrical properties of the target tissue type against values of electrical properties of the tissue type;
identifying a condition of the target tissue based on the comparison;
adjusting an energy delivery configuration of the electrosurgical treatment device to the type and condition of the target tissue; and
activating the electrosurgical treatment device to perform a treatment on the target tissue.

2. A method according to claim 1, wherein the electrode assembly is mounted on a distal end of the electrosurgical treatment device and includes a plurality of electrodes.

3. A method according to claim 1, further including the steps of measuring at least one of the electrical properties of the target tissue following the treatment; and determining the effectiveness of the treatment.

4. A method according to claim 1, wherein the electrode assembly includes a base having an electrode extending coaxially therethrough.

5. A method according to claim 4, where the coaxially extending electrode is operably connected to a high frequency generator.

6. A method according to claim 5, wherein the high frequency generator is capable of generating a frequency between 30 MHz and 30 GHz.

* * * * *